United States Statutory Invention Registration [19]

[11] Reg. Number: H708

Oka et al. [43] Published: Nov. 7, 1989

[54] METHOD OF PRODUCING DIACETONE SORBOSE

[76] Inventors: Youichi Oka, 3954-13, Oaza-murozumimura, Hikari, Yamaguchi 743; Hitoshi Sawada, 1864-11, Oaza-mitsui, Hikarai, Yamaguchi 743; Masao Yokoyama, 14-10, Nijigaoka 4-chome, Hikari, Yamaguchi 743, all of Japan

[21] Appl. No.: 35,847

[22] Filed: Apr. 8, 1987

[30] Foreign Application Priority Data

Apr. 17, 1986 [JP] Japan ..... 61-89296

[51] Int. Cl.[4] ..... C07G 3/00

[52] U.S. Cl. ..... 536/18.5; 536/18.6; 536/124

[58] Field of Search ..... 536/18.5, 124; 502/64, 502/85

[56] References Cited

U.S. PATENT DOCUMENTS

| | | | |
|---|---|---|---|
| 3,607,862 | 9/1971 | Jaffe et al. | 536/124 |
| 3,622,560 | 11/1971 | Hindley et al. | 536/124 |
| 3,723,412 | 3/1973 | Hicks et al. | 536/18.5 |
| 4,460,767 | 7/1984 | Matsumura et al. | 536/124 |
| 4,464,530 | 8/1984 | Matsumura et al. | 536/124 |
| 4,659,809 | 4/1987 | Matsumura | 536/124 |
| 4,681,936 | 7/1987 | Pfaff et al. | 536/124 |

*Primary Examiner*—John F. Terapane
*Assistant Examiner*—Richard Treanor

[57] ABSTRACT

A method of producing diacetone sorbose by reacting L-sorbose with acetone in the presence of a ketal formation catalyst in acetone, which comprises: carrying out the reaction while continuously removing water generated in the reaction together with acetone and continuously adding to the reaction mixture dehydrated acetone of which water content is not more than about 100 ppm.

6 Claims, 1 Drawing Sheet

Figure 1:
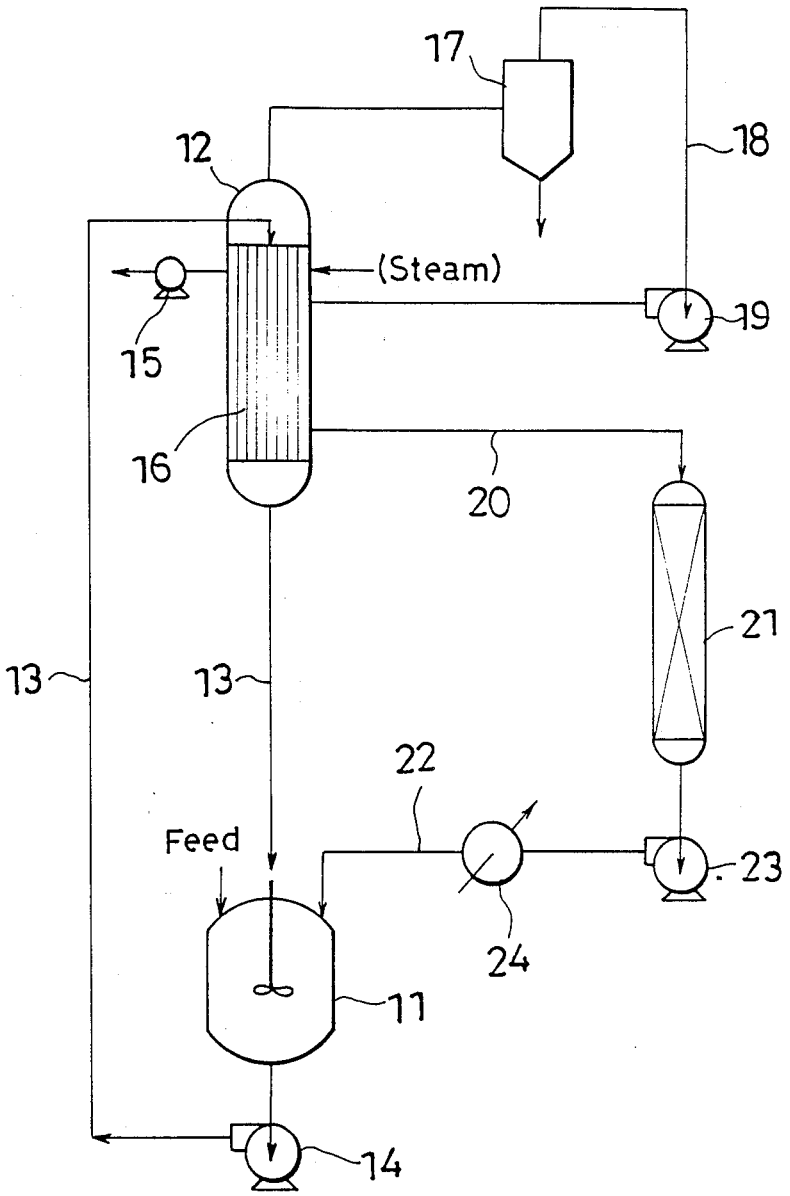

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF PRODUCING DIACETONE SORBOSE

This invention relates to a method of producing 2,3:4,6-di-O-isopylidene-L-sorbofuranose.

2,3:4,6-di-O-isopylidene-L-sorbofuranose, which is herein briefly referred of as diacetone sorbose, is an important intermediate for the production of L-ascorbic acid, and is obtained by reacting L-sorbose with acetone in the presence of a ketal formation catalyst.

A diversity of methods for producing diacetone sorbose are already known, however, all of the prior methods are attended by various defects. For instance, there is an well-known method in which concentrated sulfuric acid is used as a ketal formation catalyst. In this method, since the concentrated sulfuric acid is used also as a dehydrating agent, the acid is used in large amounts, usually in amounts of about 80–100% by weight of L-sorbose used. Therefore, the recovery of the resultant diacetone sorbose needs a step of neutralizing the sulfuric acid with a suitable alkali, and thus a step of disposal of large amounts of the resultant salts of the acid.

Since the ketal formation reaction is a dehydration condensation reaction of L-sorbose with acetone, and is an equilibrium reaction, it is already known that the removal of the water produced in the reaction improves the yields of diacetone sorbose. Therefore, a further method is known, as is described in U.S. Pat. No. 3,607,862, in which L-sorbose is reacted with acetone in the presence of perchloric acid as a ketal formation catalyst in an inert organic solvent immiscible with water such as hydrocarbons or halogenated hydrocarbons at reflux temperatures under reduced pressures, while continuously removing water produced in the reaction as azeotropic mixtures with the solvent from the reaction mixture. However, the method uses a solvent in addition to acetone, and it might have an harmful influence upon the reaction, but also the method needs installations to recover and purify the solvent as well as acetone, resulting in a high production cost of diacetone sorbose.

A further method is also known, as is described in U.S. Pat. Nos. 4,460,767 and 4,464,530 in which L-sorbose is reacted with acetone in the presence of a catalyst such as a hydrogen halide or a cupric halide while removing water generated in the reaction as a mixture thereof with acetone. However, this method also has a defect in that very large amounts of acetone must be evaporated, usually in amounts of at least about 250 times the weight of L-ascorbic acid used, to efficiently remove the reaction water from the reaction mixture. Therefore, the method needs a large scale installations, and consumes large amounts of heat energy.

Furthermore, it must be pointed out that there has been heretofore paid no full consideration to the water content of acetone used in the reaction, but commercially available acetone which contains water usually in amounts of about 1500 ppm or more has been used as it is in the reaction in the prior methods. In the two U.S. patents as referred to above, the recovered acetone is dehydrated with, for example, zeolite, and then is returned to the reaction mixture, however, it has been found out that the acetone dehydrated in the manner as described therein still contains water in amounts of at least about 300 ppm.

The inventors have made an extensive investigation to solve the problems as above, and have found out that the use of highly dehydrated acetone as additive acetone to compensate the amount of acetone removed from the reaction mixture together with the reaction water makes the amount of the catalyst and acetone needed in the reaction much smaller, and the yields of diacetone sorbose higher as well.

It is, therefore, an object of the invention to provide a method of producing diacetone sorbose which gives diacetone sorbose in higher yields by use of smaller amounts of catalysts and acetone than in the prior methods.

The method of producing diacetone sorbose by reacting L-sorbose with acetone in the presence of a ketal formation catalyst in acetone, comprises: carrying out the reaction while continuously removing water generated in the reaction together with acetone and continuously adding to the reaction mixture dehydrated acetone of which water content is not more than about 100 ppm.

According to the method of the invention, L-sorbose, acetone and a ketal formation catalyst are fed into a reactor, and the reaction is carried out at reflux temperatures preferably under reduced pressures. The amount of acetone initially fed into a reactor is usually in the range of about 6–25 times, preferably about 10–14 times the weight of L-sorbose fed into the reactor. The initial acetone may contain water in amounts of about 1500 ppm or more, and accordingly commercially available acetone is usable. However, the use of highly dehydrated acetone having an water content of not more than about 100 ppm is preferred, and acetone having an water content of not more than about 50 ppm is most preferred.

The ketal formation catalysts usable in the method of the invention are not specifically limited, and any catalyst is usable which is known in the production of diacetone sorbose, such as concentrated sulfuric acid, hydrochloric acid, perchloric acid, ferric chloride or ferric bromide; or cupric chloride or cupric bromide as described in Japanese Patent Disclosure Unexamined No. 58-55494 and U.S. Pat. No. 4,460,767; copper, iron, their oxides or salts, or hydrogen halides as described in Japanese Patent Disclosure Unexamined No. 58-167583 and U.S. Pat. No. 4,460,767 iodine or hydrogen iodide as described in Japanese Patent Disclosure Unexamined No. 58-167582 and U.S. Pat. No. 4,464,530; or antimony pertafluoride or antimony pentachloride as described in Japanese Patent Disclosure Unexamined No. 60-69092 and European Patent Publication No. 0 139 487. Among these catalysts are especially preferred concentrated sulfuric acid, perchloric acid, iodine or hydrogen iodide.

According to the invention, the catalyst may be used in smaller amounts than in the prior methods. For instance, concentrated sulfuric acid may be used in amounts of about 3–10% by weight of L-sorbose used, namely the amount is about one tenths times or less the amount used in the prior methods where hydrous acetone containing about 1500 ppm or more of water is used. When perchloric acid, iodine or hydrogen iodide is used, the amount thereof may be in the same range as that used in the prior methods, however, diacetone sorbose may be produced in the same yields as in the prior methods even by use of the catalyst in amounts of about one fifths times the amount used in the prior methods under the otherwise same reaction conditions.

According to the invention, the reaction is carried out while continuously removing the water produced in the reaction, i.e., the reaction water, together with acetone, and at the same time continuously adding highly dehydrated additive acetone which has an water content of not more than about 100 ppm, preferably about 50 ppm, to the reaction mixture. As described hereinbefore, the commercially available acetone contains water usually in amounts of about 1500 ppm or more. It is dehydrated to a water content of not more than about 100 ppm, preferably to not more than about 50 ppm, whereupon it is usable as the additive acetone in the invention. For this purpose, the commercial acetone may be dehydrated preferably with zeolite which has pores of about 3 Angstrom in average diameter and contains water in amounts not more than about 4% by weight.

The zeolites usable are not specifically limited, however, such zeolites as have been activated by treating with air or inert gases such as nitrogen, carbon dioxide or argon at temperatures of about 200°-300° C. are preferably used. By way of example, the zeolite thus treated is placed in a column in amounts in accordance with the amount and the water content of hydrous acetone to be dehydrated, and the hydrous acetone is passed through the column, to provide highly dehydrated acetone. When a zeolite which has an water adsorption power of 10% by weight is used, for example, the amount needed is about 20 times the breaking load of dehydration so as to provide highly dehydrated acetone.

A column used has preferably a cross section so that hydrous acetone may pass therethrough at a linear velocity of 2–4 m/hr, and the hydrous acetone is passed through the column at a space velocity preferably of not more than about 2 so that the hydrous acetone is effectively contacted with the zeolite.

According to the invention, the reaction water is removed as a mixture of the water with acetone from the reaction mixture by distillation, and such a distillate of the mixture of the water with acetone, i.e., hydrous acetone, usually contains water in very small amounts, for example, in amounts of about 200–5000 ppm. Therefore, the rate of the removal of the water from the reaction mixture may be determined by the rate at which the hydrous acetone is distilled off from the reaction mixture in industrial application of the invention, while dehydrated additive acetone is added to the reaction mixture in a rate approximately corresponding to the rate at which the hydrous acetone is distilled off, preferably at a rate substantially the same as the rate of distillation of the hydrous acetone, as is described hereinafter.

When the reaction water is removed as a mixture thereof with acetone as above, as the rate of the removal of the hydrous acetone becomes higher, the reaction rate becomes higher, but at the same time, the efficiency of the removal of the water becomes smaller, so that it is necessary that the hydrous acetone be removed at a suitable rate. Therefore, the hydrous acetone is distilled off preferably at a rate of about 0.5–2 times the initial amount of the acetone fed into a reactor per hour, and most preferably at a rate of about 0.8–1.2 times.

It is also necessary that while the hydrous acetone which contains the reaction water is continuously removed from the reaction mixture as above, dehydrated acetone of which water content is not more than about 100 ppm be continuously added to the reaction mixture at a rate which is approximately corresponding to the rate at which the hydrous acetone is distilled off from the reaction mixture. The rate of the removal of the hydrous acetone is preferably substantially the same as the rate of distillation of the hydrous acetone, thereby to keep the concentration of the reaction mixture substantially constant.

The reaction temperatures and pressures are so selected that the water formed in the reaction is removed efficiently. The temperature is preferably about 30°-50° C. and the pressure is preferably about 300–500 Torr. Most preferably the reaction is carried out at temperatures of about 40°–45° C. under reduced pressures of 400–450 Torr.

In carrying out the reaction in accordance with the method of the invention, the vapor recompression system is advantageously adopted to remove the reaction water together with acetone. The system per se is already well known as a system in which a vapor generated in an evaporator is recompressed to utilize to heat the vapor itself. The application of the system to the production of diacetone sorbose is fully described in the common assignee's preceding U.S. Pat. application Ser. No. 788,433.

The single drawing illustrates an example of an apparatus system diagram for carrying out the reaction according to the method of the invention wherein the vapor recompression system is made use of.

The apparatus includes a reactor 11 and an evaporator 12 which is connected to the reactor through a circulating pipe 13 equipped with a circulating pump 14. The evaporator has a vacuum pump 15 connected thereto and may be, for example, a plate type evaporator which is provided with a heating means such as plates 16 therein. The reactor, the evaporator and the pipe thus form a loop circuit for circulation of the reaction mixture. The evaporator 12 is communicating with a gas-liquid separator 17, which is communicating with the plates 16 through a vapor pipe 18 equipped with a compressor 19. The plates are at the lower part connected through a condensate pipe 20 to a dehydrator 21, which is in turn connected to the reactor 11 through a return pipe 22 equipped thereon with a pump 23 and a preheater 24. The reactor, the separator, the dehydrator and the plates thus form a vapor recompression and acetone circulating system.

At the outset of the reaction, L-sorbose, acetone and a ketal formation catalyst are fed into the reactor, and mixed together therein. Then the vacuum pump 15 is operated to reduce the pressure inside the evaporator and the reactor to a predetermined value. Then the reaction mixture is circulated between the reactor and the evaporator through the beforesaid loop with the pump 14, and at the initial stage of the reaction, steam, for example, is supplied into the plates of the evaporator to heat the reaction mixture therein, thereby to start the reaction.

The temperature of the mixture gradually increases in this way, whereupon the reaction starts, and part of acetone and water formed during the reaction begin to evaporate together. The amount of the vapor gradually increases as the reaction proceeds, to heat the separator and the compressor. When the temperature has reached a sufficient level to enable the compressor to operate, the supply of the steam to the plates of the evaporator is discontinued, while the vapor, alter having been subjected to the gas-liquid separation in the separator 17, is supplied into the plates to heat the reaction mixture in the evaporator 17. In this way, the apparatus system functions as a reactor and evaporator of the vapor recompression type, to allow the reaction to proceed in a stable and steady manner.

The vapor produced in the evaporator is a mixture of vapors of acetone and the reaction water, and it contains water in amounts usually of about 200–5000 ppm, although varying depending upon the reaction conditions. The vapor is then subjected to the gas-liquid separation in the separator, as described hereinbefore, and then is pressurized in the compressor, which may be of the Roots type or of the turbo type, for instance. The vapor, now with an increased enthalpy, is fed into the plates of the evaporator, to supply heat to the reaction mixture, and then is introduced, usually as a drain, to the dehydrator 21.

The compression rate of the vapor is selected depending upon the elevation of boiling points of the reaction mixture, the mechanical efficiency in the vapor compression and other factors. However, the compression rate is generally not more than about 2, and the rate of about 1.4–1.6, for example, is preferable in most cases.

The reaction is continued in a stable and steady manner by supplying dehydrated additive acetone whose water content is not more than about 100 ppm, preferably not more than about 50 ppm, at a rate approximately corresponding to the rate at which acetone is removed as hydrous acetone from the reaction mixture, to the evaporator via the return pipe 23 with the pump 23 and the preheater 24.

In the invention it is advantageous to dehydrate the drain, i.e., hydrous acetone, in the dehydrator so as to provide highly dehydrated acetone to an water content of not more than about 100 ppm, preferably of not more than about 50 ppm, and to add this dehydrated acetone as an additive acetone to the reaction mixture from the viewpoint of industrial process economy. The hydrous acetone may be dehydrated to such levels as above by use of, for example, zeolite, as described hereinbefore.

Various types of vapor recompression systems may be adopted in the invention. For instance, plate or tubular type evaporators may be used. Also the manners in which the reaction mixture is circulated may be selected suitably in consideration of the characters of the reaction and the properties of the reaction mixture. For instance, the reaction mixture may he forced to flow downwardly in the evaporator or allowed to spontaneously flow downwardly. It is also possible to control the concentrations of the reaction mixture and the rates of the reaction by adjusting the amount of the dehydrated acetone to the reaction mixture.

According to the invention, the reaction may be carried out in a continuous manner while continuously removing the water together with acetone, or may be carried out in a batchwise manner.

After the completion of the reaction, diacetone sorbose may be recovered and purified in conventional manners. By way of example, an amount of alkali such as sodium hydroxide of about 1.1 times the equivalent to the acid used in the reaction is added to the resultant reaction mixture, acetone is distilled off therefrom, the resultant aqueous solution is extracted with benzene, and the extract is concentrated to dryness, to give crystals of diacetone sorbose.

As set forth above, the invention is featured in the use of acetone of which water content is not more than about 100 ppm, and the invention makes in possible to produce diacetone sorbose in higher yields by using a smaller amount of acetone and a ketal formation catalyst.

For instance, when concentrated sulfuric acid is used as a ketal formation catalyst, the amount thereof is reduced to about one tenths times or less the amount used in the prior methods, and furthermore the water formed in the reaction is more readily removed from the reaction system. Therefore, the method of the invention needs only a very small amount of alkalis to neutralize the acid after the reaction, and hence produces only a very small amount of the salts, so that the method makes the recovery and purification of the product very easy and feasible.

Moreover, the method permits an efficient removal of the reaction water together with acetone, and therefore, when perchloric acid, for example, is used as a ketal formation catalyst, the amount of acetone needed is smaller than in the prior methods. As a further advantage, there is no need of azeotropic distillation of the reaction water according to the invention. Still further, even when the other catalysts are used, the yields of diacetone sorbose are remarkably improved.

The invention will be more easily understood with reference to the following examples, which however are intended to illustrate the invention only and are not to be construed as limiting the scope of the invention.

EXAMPLE 1

An amount of 1.5 l of zeolite (Zeoram 3AGS by Toyo Soda K.K., Japan) was spreaded thinly on a metal plate, air dried for 1 day, and then heated in an electric dryer at a temperature of 230° C. for 7 hours, to provide zeolite containing 2% by weight of water. After cooling, 1100 g of the zeolite was filled in a column of 30 mm in diameter and 2000 mm in height, and 15 l of commercial acetone containing water in amounts of 2000 ppm were passed through the column at a space velocity of 2, to provide highly dehydrated acetone containing water in amounts of 40 ppm.

An amount of 1400 ml of the dehydrated acetone, 100 g of L-sorbose and 4 ml of concentrated sulfuric acid were placed in a 3 l-capacity flask, and the pressure inside of the flask was reduced to 480 Torr. Then the flask was placed in an water bath at 45° C. for 10 hours while adding thereinto the dehydrated acetone at a rate of about 1.25 l per hour and removing the hydrous-acetone therefrom by distillation at a rate of about 1.25 l per hour.

After the completion of the reaction, the resultant reaction mixture was neutralized with a 30% aqueous solution of sodium hydroxide in amounts of 1.1 times the amount of the sulfuric acid used, and then the acetone in the mixture was distilled off. The resultant aqueous solution was then extracted with benzene, to provide a benzene solution of diacetone sorbose, followed by the evaporation of the solution to dryness, to provide 127.1 g (88.0% yield) of diacetone sorbose.

EXAMPLE 2

The reaction was carried out at temperatures of 30° C., 35° C. or 40° C. for 12 hours, and the otherwise in the same manner as in Example 1, to provide diacetone sorbose. The yields are 86.4%, 86.0% and 88.6%, respectively.

COMPARATIVE EXAMPLE 1

Commercial acetone (Wako Junyaku Kogyo K.K., Japan) containing 1800 ppm of water was used as an additive acetone in place of the dehydrated acetone, and the reaction was carried out otherwise in the same manner as in Example 1, to provide 113.5 g (78.6% yield) of diacetone sorbose.

COMPARATIVE EXAMPLE 2

An amount of 100 g of L-sorbose, 1400 ml of hydrous acetone containing water in amounts of 1500 ppm, and 30 ml of concentrated sulfuric acid were placed in a 3 l-capacity flask. The mixture was reacted at 30° C. under stirring and under a reduced pressure for 1.5 hours in the same manner as in Example 1 except that the same hydrous acetone as above was used as an additive acetone, to provide 94.6 g (65.5% yield) of diacetone sorbose.

When the concentrated sulfuric acid was used in amounts of 53 ml in the above reaction, 115.5 g (80.0% yield) of diacetone sorbose was obtained.

EXAMPLE 3

An amount of 1400 ml of acetone containing 35 ppm of water, 100 g of L-sorbose and 0.44 ml of a 61% perchloric acid solution containing 0.4 g of perchloric acid were placed in a 3 l-capacity flask provided with a stirrer and a cooling tube. The mixture was then reacted at 45° C. for 9 hours under a reduced pressure while adding an additive acetone containing 35 ppm of water to the reaction mixture at a rate of 1.25 l per hour and at the same time distilling off the hydrous acetone generated at a rate of 1.25 l per hour.

After completing the reaction, 4 ml of a 30% aqueous solution of sodium hydroxide were added to the reaction mixture to neutralize the perchloric acid, the acetone was distilled off to provide an aqueous solution, followed by the extraction thereof with benzene, to provide a benzene solution of diacetone sorbose. The solution was evaporated to dryness, to provide 131.0 g (90.7% yield) of diacetone sorbose.

EXAMPLE 4

An amount of 1.2 g of iodine as a catalyst and dehydrated acetone containing 50 ppm of water were used, and the reaction was carried out otherwise in the same manner as in Example 3, to provide 128.1 g (88.7% yield) of diacetone sorbose.

COMPARATIVE EXAMPLE 3

An amount of 200 ml of commercial hydrous acetone containing water in amounts of 1500 ppm, 10.0 g of L-sorbose and 127 mg of iodine were placed in a reactor provided with a cooling tube and a drying tube of 2 cm in diameter and 13 cm in length interposed between the reactor and the cooling tube. The drying tube had 30 g of Molecular Sieves 3A (Wako Junyaku Kogyo K.K., Japan) filled therein to dehydrate refluxed solvent during the reaction.

After the completion of the reaction, 0.5 ml of a 30% aqueous solution of sodium hydroxide were added to the reaction mixture, and then acetone was distilled off to provide an aqueous solution. The aqueous solution was then extracted with benzene, to provide a benzene solution of diacetone sorbose, followed by the evaporation of the solution to dryness, to provide 12.1 g (83.8% yield) of diacetone sorbose.

The water contents of acetone dehydrated in the drying tube and returned to the reaction mixture are shown in Table 1 at every one hour.

TABLE 1

| Reaction Time (hr) | Water Contents of Acetone Returned (ppm) |
|---|---|
| 1 | 310 |
| 2 | 670 |
| 3 | 600 |
| 4 | 720 |
| 5 | 830 |
| 6 | 770 |

EXAMPLE 5

An amount of 740 kg of Zeoram 3AGS was placed in a column of 1000 mm in diameter and 1700 mm in height and treated with 500 $Nm^3$ of nitrogen at 230° C. for 4.5 hours.

Hydrous acetone having water contents in the range of 200–3000 ppm was passed through the column at a rate of 1500 l per hour, namely at a space velocity of 1.5 and a linear velocity of 2 m/hour, to provide 6325 l of highly dehydrated acetone whose water content was not more than 50 ppm.

In this Example, there was used an apparatus system including a reactor, a plate type evaporator and a compressor so connected as to form a vapor recompression type evaporator, as shown in the drawing.

An amount of 50 kg of L-sorbose was fed into the reactor together with 700 l of the acetone as dehydrated as above and 0.6 kg of iodine. For initiating the reaction, steam was supplied into the plates of the plate type evaporator at a pressure of 1.9 $kg/cm^2G$ while circulating the mixture between the reactor and the evaporator.

The temperature inside the plates of the evaporator reached 55.5° C. in about 60 minutes, and then hydrous acetone was distilled off at a rate of about 500 kg/hr which was found to contain water in amounts of about 200–3000 ppm, while the dehydrated acetone as obtained above was healed to about 46° C. and supplied into the evaporator at substantially the same rate at which the acetone was distilled off from the reaction mixture. The reaction was carried out in this way at a temperature of 46° C. for 9 hours.

After the completion of the reaction, the resultant reaction mixture was cooled and neutralized, acetone was distilled off, and the resultant solution was extracted with benzene, followed by the removal of benzene from the solution to provide 63.5 kg (88.0% yield) of diacetone sorbose as a residue.

What is claimed is:

1. A method of producing diacetone sorbose by reaction of L-sorbose with acetone in the presence of a ketal formation catalyst in acetone in a reactor, which comprises feeding into the reactor L-sorbose, acetone which has been dehydrated with zeolite activated at a temperature of 200°–300° C. and has a water content of not more than about 50 ppm in an amount of about 6–25 times the weight of the L-sorbose, and a ketal formation catalyst of the class consisting of concentrated sulfuric acid, perchloric acid and iodine, and carrying out the reaction of the L-sorbose with the acetone at reflux temperatures under reduced pressures, while continuously removing water formed in the reaction as a mixture with acetone by distillation at a rate of amounts of about 0.5–2 times the weight of the amount of the acetone initially fed into the reactor per hour and continuously adding to the reaction mixture dehydrated acetone of a water content not more than about 50 ppm at a rate corresponding approximately to the rate at which the mixture of water and acetone is removed from the reaction mixture.

2. The method as claimed in claim 1 wherein the reaction is carried out in the presence of concentrated sulfuric acid in amounts of about of 3–10% by weight of L-sorbose.

3. The method as claimed in claim 1 wherein the reaction is carried out at temperatures of about 30°–50° C. under reduced pressures of about 300–500 Torr.

4. The method as claimed in claim 3 wherein the reaction is carried out at temperatures of about 40°–45° C. under reduced pressures of about 400–450 Torr.

5. The method as claimed in claim 1, wherein the reaction is carried out by use of an apparatus system which includes a reactor and an evaporator connected thereto so that the reaction mixture may circulate therebetween, and a compressor connected both to the evaporator and a heating means for the evaporator, wherein a vapor of the mixture of the water with acetone generated in the evaporator is compressed and supplied to the heating means to heat the reaction mixture.

6. The method as claimed in claim 5 wherein the apparatus system further includes a dehydrator which is connected both to the heating means and the reactor, wherein the condensate of the vapor is dehydrated in the dehydrator to a water content of not more than about 100 ppm, and then is returned to the reactor.

* * * * *